United States Patent
Li

(10) Patent No.: US 8,241,522 B2
(45) Date of Patent: Aug. 14, 2012

(54) LIQUID CRYSTALLINE BLENDS, DEVICE THEREOF AND METHOD THEREOF

(75) Inventor: Quan Li, Stow, OH (US)

(73) Assignee: Kent State University, Kent, OH (US)

( * ) Notice: Subject to any disclaimer, the term of this patent is extended or adjusted under 35 U.S.C. 154(b) by 285 days.

(21) Appl. No.: 12/597,940

(22) PCT Filed: Jul. 30, 2009

(86) PCT No.: PCT/US2009/052184
§ 371 (c)(1),
(2), (4) Date: Oct. 28, 2009

(87) PCT Pub. No.: WO2010/047864
PCT Pub. Date: Apr. 29, 2010

(65) Prior Publication Data
US 2011/0023946 A1    Feb. 3, 2011

Related U.S. Application Data

(60) Provisional application No. 61/107,386, filed on Oct. 22, 2008.

(51) Int. Cl.
*C09K 19/52* (2006.01)
*C09K 19/32* (2006.01)
*C09K 19/34* (2006.01)
*C09K 19/54* (2006.01)
*H01L 51/00* (2006.01)
*H01L 31/042* (2006.01)
*H01L 35/24* (2006.01)

(52) U.S. Cl. ........... 252/299.01; 252/299.5; 252/299.61; 252/299.62; 438/30; 438/60; 438/99; 257/40; 136/263

(58) Field of Classification Search ............. 252/299.01, 252/299.5, 299.61, 299.62; 438/97, 30, 60, 438/99; 257/40; 136/263
See application file for complete search history.

(56) References Cited

U.S. PATENT DOCUMENTS
7,291,727 B1    11/2007    Li et al.

FOREIGN PATENT DOCUMENTS
EP    1 722 424 A1    11/2006

OTHER PUBLICATIONS

International Search Report for International Application No. PCT/US2009/52184, Completed, Completed Aug. 28, 2009. Written Opinion of the International Searching Authority for International Application No. PCT/US2009/52184, Completed Aug. 28, 2009.
Lloyd, M.T.; Mayer, A.C.; Subramanian, S.; Mourey, D.A.; Herman, D.J.; Bapat, A.V.; Anthony, J.E. and Malliaras, G.G., Efficient Solution-Processed Photovoltaic Cells Based on an Anthradithiophene/Fullerene Blend. J. Am. Chem. Soc., 2007, 129, 9144-9149.

*Primary Examiner* — Shean Wu

(74) *Attorney, Agent, or Firm* — Fay Sharpe LLP

(57) ABSTRACT

The invention provides liquid crystalline blends, a device such as a photovoltaic cell using the blend and method thereof. A liquid crystalline blend comprises at least an electron donor and at least an electron acceptor with a weight or molar ratio in the range of from about 1:20 to about 20:1. Another liquid crystalline blend comprises at least an electron donor and at least an electron acceptor, wherein the electron donor, the electron acceptor, or both is (are) halo-substituted such as F-substituted. The donor or the electron acceptor can be excited by an electromagnetic radiation such as solar light to induce electron transfer between the donor and the acceptor. The photovoltaic cell is improved in that favorable molecular arrangement in the blend gives more interfaces between the donor and the acceptor and thus a viable path for dissociation and electrons and/or holes; as well as larger light-harvesting area toward the coming light.

34 Claims, 1 Drawing Sheet

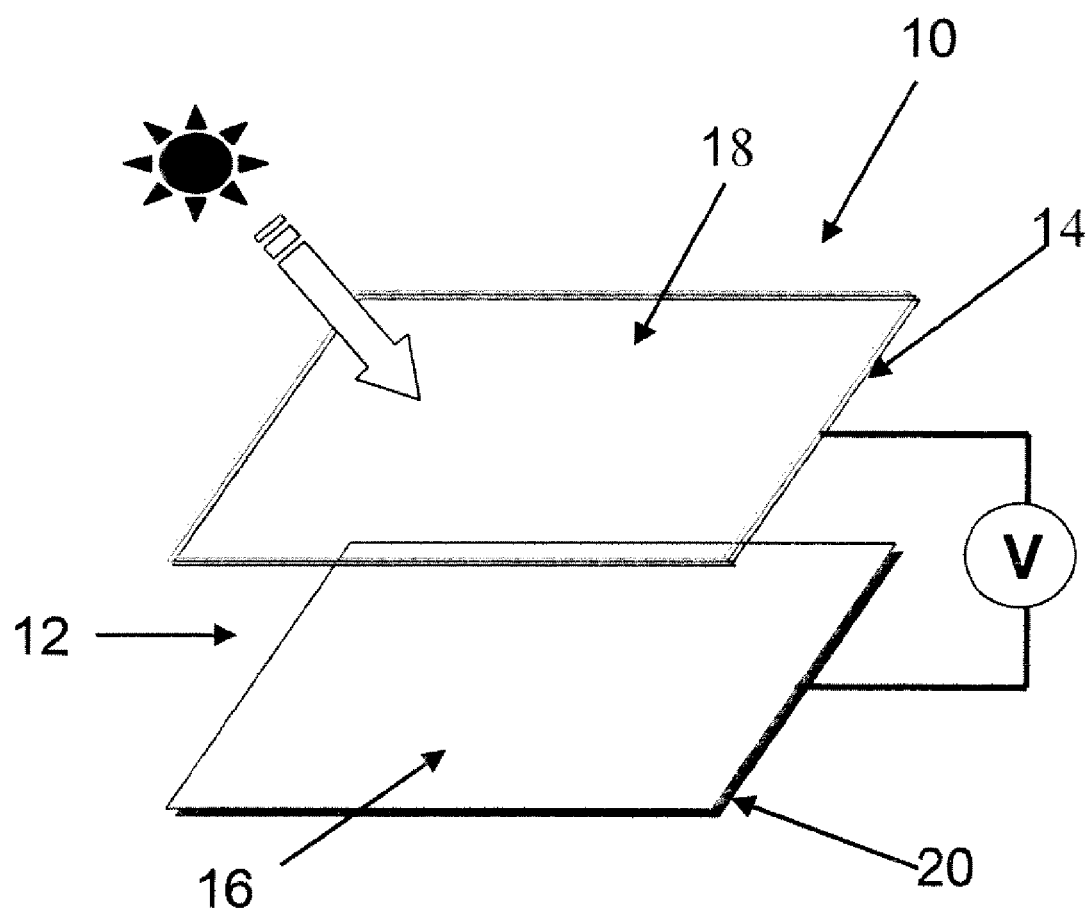

LIQUID CRYSTALLINE BLENDS, DEVICE THEREOF AND METHOD THEREOF

This application claims the priority of the U.S. provisional application with the application No. 61/107,386, which was filed on Oct. 22, 2008.

BACKGROUND OF THE INVENTION

The present invention is related to liquid crystalline blends, devices thereof and methods thereof. It finds particular application in conjunction with an organic semiconducting material, a photovoltaic device such as a bulk heterojunction photovoltaic cell, a solar cell, a homeotropically aligned blend thin film, a liquid crystalline blend thin film, a photo-sensitive electric resistor, and an organic light emitting device; and will be described with particular reference thereto. However, it is to be appreciated that the present exemplary embodiment is also amenable to other like applications.

In the long term, solar energy is the only source of renewable energy that has the capacity to fill humanity's technological needs. A grand challenge is to convert solar energy into green electric energy in an inexpensive and efficient way. The crystalline silicon photovoltaic cells, though efficient, appear to be too expensive to compete with primary fossil energy.

Organic photovoltaic (OPV) technology would hold a great promise for the cost reduction since the OPV materials are potentially cheap, easy to process, and capable of being deposited on flexible substrates such as plastics and bending where their inorganic competitors e.g. crystalline silicon would crack. Currently widely used OPV materials, e.g. Cu phthalocyanine, suffer from the scattering of electron/exciton between small crystal grain boundaries in which random arrangement of molecules results in poor charge mobility. The attainment of large-area single crystals or desired molecular arrangement of either inorganic (e.g. silicon) or organic molecules is difficult and costly to process although a crystalline phase has superior properties compared to the same material in an amorphous phase. A challenge for OPV, with the possibility of very significant cost reduction, is to make them in desired macroscopic order to improve charge transportation etc. One route to overcoming this problem is to synthesize OPV materials that exhibit liquid crystal (LC) phases since LCs are typically "soft", i.e., they respond easily to external stimuli and their alignment could be manipulated by external fields and surface effects. LC systems are unique in their partial ordering. In the LC state, these materials are able to self-repair any misorientations and structural defects, which could result in obtaining ordered thin films essential for highly efficient photovoltaic devices.

Organic and polymer semiconducting materials usually have an approximately 10 nm exciton diffusion range. So, only the excitons close to the donor-acceptor interface in a donor and acceptor bilayer photovoltaic cell can contribute to the photocurrent, which dramatically limits photovoltaic performance. Compared with a donor and acceptor bilayer PV cell, a blend made from an electron-donor component and an electron-acceptor component can offer a much larger interface between donor and acceptor as a result of an efficient dissociation of excitons in the supramolecular arrangement.

An important improvement on the performance in polymer photovoltaic cells has been demonstrated by mixing an electron donor component (p-type semiconducting material) with an electron acceptor component (n-type material). However, one challenge that remains for OPV technology, with the possibility of very significant cost reduction, is to make them in desired macroscopic order to improve charge transportation.

It is well established that discotic LCs as active components in high efficient photovoltaic (PV) cells are critically dependent on the supramolecular arrangement of the blend made from at least an electron donor component and at least an electron acceptor component. In order to make a discotic LC with more efficient absorption of sunlight, one should consider porphyrin as the building block of the potentially most viable discotic material since it is the basic structure of the best photoreceptor in nature, chlorophyll. Porphyrin and its derivatives have many desirable features such as highly conjugated plane, high stability, intense absorption of sunlight, and the small gap between the highest occupied molecular orbital (HOMO) and lowest unoccupied molecular orbital (LUMO) energy level.

However, to date there is no report on the alignment of discotic LC (such as porphyrin)-fullerene blend or fluorinated LC-fullerene blend, particularly when the ratio between the two is in the range of 1:20 to 20:1. Advantageously, the present invention provides a liquid crystalline blend, a device made using the same and a method of making the same, which meet this need, wherein the LC blend and the device incorporating the LC blend exhibit merits such as favorable molecular arrangement with more interface between electron donating material and electron accepting material, and a viable path for dissociation and electrons and/or holes, among others.

BRIEF DESCRIPTION OF THE INVENTION

One aspect of the invention provides a liquid crystalline blend comprising at least an electron donor and at least an electron acceptor, wherein the weight or molar ratio between the electron donor and the electron acceptor is in the range of from about 1:20 to about 20:1; and the electron donor or the electron acceptor can be excited by an electromagnetic radiation to induce electron transfer between the electron donor and the electron acceptor.

Another aspect of the invention provides a liquid crystalline blend comprising at least an electron donor and at least an electron acceptor, wherein the electron donor, the electron acceptor, or both is (are) halo-substituted such as F-substituted; and the electron donor or the electron acceptor can be excited by electromagnetic radiation to induce electron transfer between the electron donor and the electron acceptor.

Still another aspect of the invention provides various materials and devices such as an organic semiconducting material, a photovoltaic device such as a bulk heterojunction photovoltaic cell, a solar cell, a homeotropically aligned blend thin film, a liquid crystalline blend thin film, a photo-sensitive electric resistor, and an organic light emitting device, which comprise one of the liquid crystalline blends as described above.

Yet another aspect of the invention provides various methods for producing a photovoltaic cell, featured with a step of placing a liquid crystalline blend between two electrodes, wherein the liquid crystalline blend is selected from the liquid crystalline blends as described above.

BRIEF DESCRIPTION OF THE DRAWINGS

FIG. 1 schematically illustrates a photovoltaic cell using a liquid crystalline blend according to an embodiment of the invention.

DETAILED DESCRIPTION OF THE INVENTION

Any particular theory that is used in the description, as an attempt to academically understand the mechanism of the invention, should not be interpreted as limitative to the scope of the invention.

In various exemplary embodiments, the weight or molar ratio between the electron donor and the electron acceptor in the liquid crystalline blend of the invention is generally in the range of from about 1:20 to about 20:1, preferably in the range of from about 1:10 to about 10:1, more preferably in the range of from about 1:6 to about 6:1, and most preferably in the range of from about 1:2 to about 2:1.

In various exemplary embodiments, the electron donor, the electron acceptor or both in the liquid crystalline blend is (are) halo-substituted such as F-substituted, Cl-substituted, Br-substituted, and I-substituted. For example, the electron donor may be F-substituted.

In various embodiments, the electromagnetic radiation used to excite the electron donor, the electron acceptor or both in the liquid crystalline blend can be selected from gamma ray, X-ray, UV-Visible light, infrared radiation, and any combination thereof. In preferred embodiments, the electromagnetic radiation comprises solar light. The donor, acceptor, or both can be photo-excited and then drive the electron transfer between them. In a specific embodiment, the donor is photo-excited.

In various exemplary embodiments, a plurality of the electron donor, a plurality of the electron acceptor, or both can be self-assembled or self-organized. For example, donors such as discotic liquid crystalline porphyrins, discotic liquid crystalline phthalocyanines and their metal complexes can be aligned into an ordered architecture, in which the columns formed by intermolecular stack are spontaneously perpendicular on the surface, i.e. homeotropic alignment. The aligned architecture, which is stable within a wide temperature range, can greatly enhance the charge carrier mobility, and thus can dramatically improve the light induced electric generation.

In an embodiment, the liquid crystalline blend can exhibit a columnar liquid crystal phase which is partially or completely homeotropically aligned under proper conditions such as temperature. Thus, the embodiment can provide a homeotropically aligned discotic liquid crystal-fullerene blend for use in a device such as a bulk heterojunction photovoltaic device.

In typical embodiments, the electron donor, the electron acceptor, or both may comprise a π-conjugated structure. Requirements for the molecular design of the donor and/or acceptor, if used to absorb electromagnetic radiation such as solar light, include, but are not limited to, high molecular conjugation, proper HOMO and LUMO, and strong absorption in the solar spectrum.

Examples of the electron donor include, but are not limited to, a porphyrin-based compound, a phthalocyanine-based compound, a polymer, and any combination thereof. Examples of the electron acceptor include, but are not limited to, a fullerene-based compound, a carbon nanotube, a graphene, a photosensitive dye, and any combination thereof. For efficient absorption of radiation such as sunlight it is logical to use porphyrin as the building block of discotic materials since it has the basic structure of the best photoreceptor in nature, chlorophyll. Porphyrin and its derivatives have many desirable features, such as a highly conjugated disc plane, high stability, efficient absorption of sunlight and a small gap between the highest occupied molecular orbital (HOMO) and lowest unoccupied molecular orbital (LUMO) energy levels.

In specific embodiments, the electron donor comprises a compound selected from the group consisting of a porphyrin-based compound, a phthalocyanine-based compound, and any combination thereof. The electron acceptor comprises a fullerene-based compound. The weight or molar ratio between such electron donor and such electron acceptor is in the range of from about 1:6 to about 6:1, preferably in the range of from about 1:2 to about 2:1. For example, it has been discovered that some synthesized liquid crystal porphyrins according to the invention can be mixed with a $C_{60}$ derivative (PCBM) or $C_{70}$ derivative ($PC_{71}BM$), graphene, and the resulting blend can be homeotropically aligned. The invention provides a homeotropic alignment of nanoscale liquid crystalline porphyrin, i.e., the columns formed by intermolecular π-π stacking are spontaneously perpendicular to the substrate, and the recurrence of homeotropic alignment for porphyrin doped with fullerene material such as 1-(3-methoxycarbonyl)propyl-1-phenyl-(6,6)$C_{61}$ (PCBM) through maintaining its liquid crystal phase.

In exemplary embodiments, the blend of the invention comprises at least a discotic liquid crystal as an electron donating material and a fullerene material such as $C_{60}$, $C_{60}$ derivative, $C_{70}$ or $C_{70}$ derivative as an electron accepting material, which is capable of being used as a highly efficient photovoltaic device. A large π-conjugated discotic LC, such as discotic porphyrin and phthalocyanine, is a superior electron donor, whereas fullerene (e.g. $C_{60}$ or its derivative) is an excellent electron acceptor.

Discotic liquid crystals (LCs) as active components in high efficient photovoltaic (PV) cells are critically dependent on the supramolecular arrangement of the blend made from an electron donor component and an electron acceptor component. The discotic LC, such as discotic porphyrin and phthalocyanine, is a superior electron donor, whereas fullerene (e.g. $C_{60}$ or its derivative) is an excellent electron acceptor. Homeotropically aligned blends consisting of at least a discotic liquid crystal as an electron donating material and at least a fullerene material, such as $C_{60}$ or $C_{60}$ derivative, as an electron accepting material are extremely important for e.g. high efficient photovoltaic devices, since this favorable molecular arrangement with more interface can provide a viable path for dissociation and electrons and/or holes along the columnar axis, and the light-harvesting molecules are arranged with the largest area toward the coming light.

For example, the porphyrin-based compound may comprise a Formula (I) compound, and the phthalocyanine-based compound may comprise a Formula (II) compound:

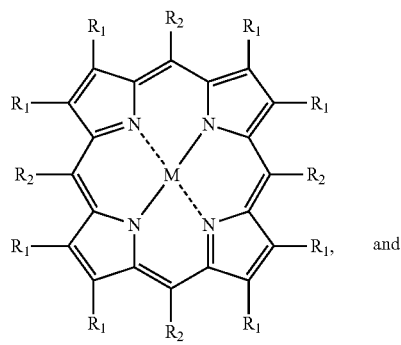

(I)

and

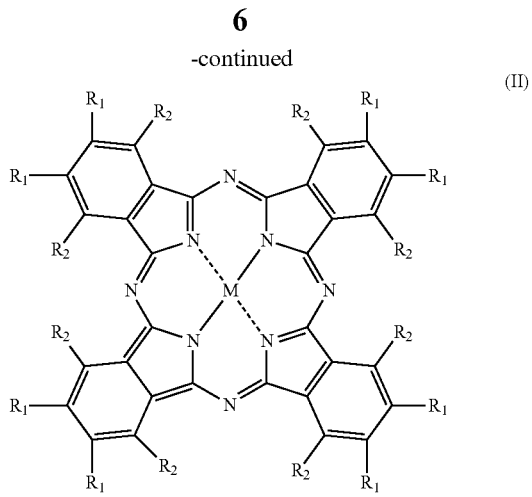

(II)

wherein M=2H, Zn, Co, Cu, Ni, Cr, Mn, Mg, Ce, Ru, Rh, Pt, Au, or a lanthanide metal and which may be bound to halo, O, OH, =CO, amine or heterocylic moiety; and wherein each of $R_1$ and $R_2$ independently of each other comprises an alkyl which may optionally include any perfluoroalkyl, substituted $C_{60}$ moiety, aromatic moiety, heterocyclic moiety, or one or more of O, Br, Cl, S, CO, COO, NH, C≡C, N=N and/or C=C.

In some embodiments, the porphyrin-based compound may comprise a Formula (III) compound, and the phthalocyanine-based compound may comprise a Formula (IV) compound:

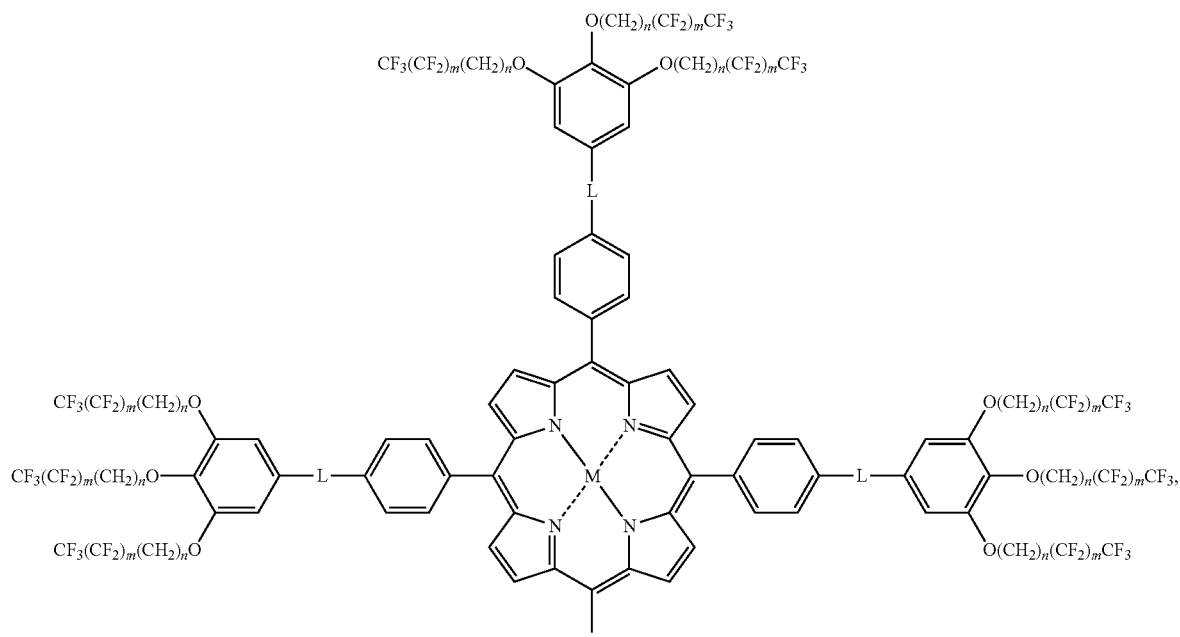

(III)

-continued

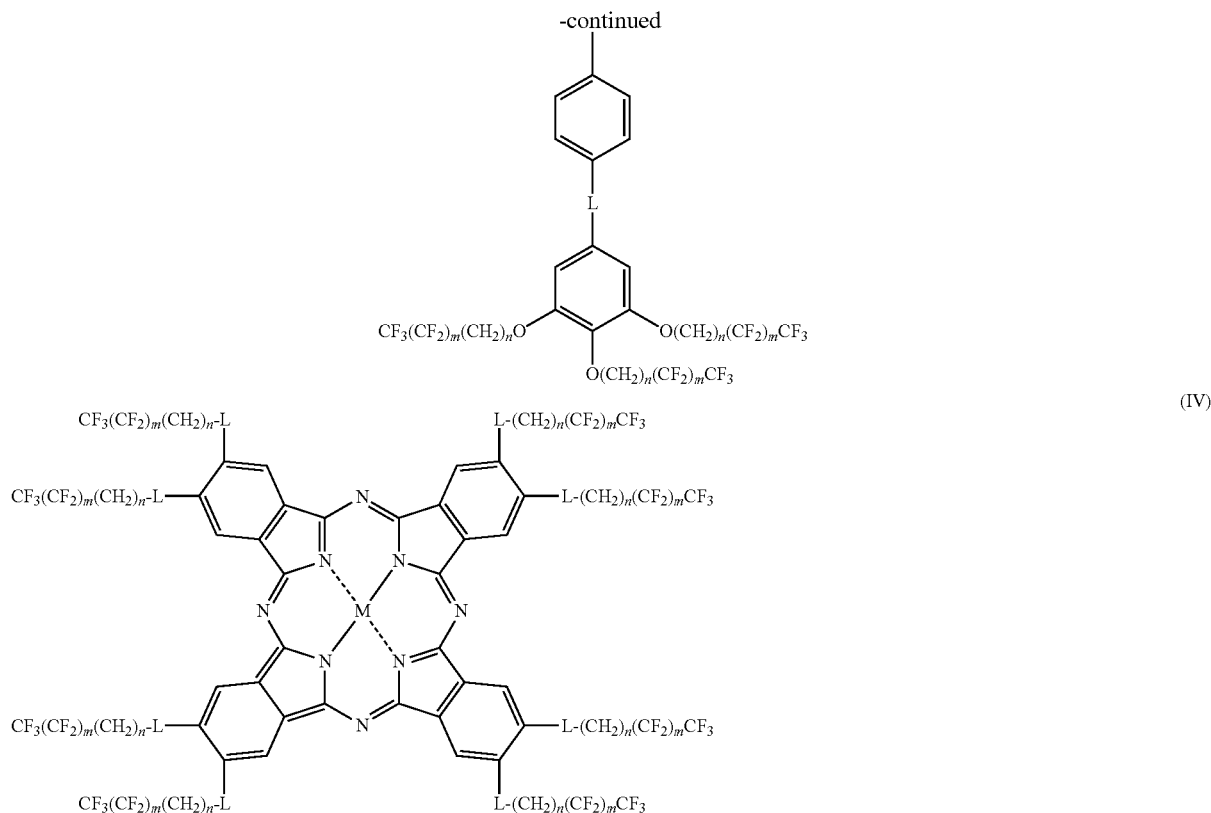

(IV)

wherein m is in the range of 0-20, n is in the range of 3-20, and M is selected from 2H, Cu, Zn, Mg, Co, Ni, Mn, Fe, Ce, Ru, Rh, Pt, Au, or a lanthanide metal and which may be bound to halogen, O, OH, =CO, amine or a heterocyclic moiety, and L is a linking group selected from COO, OOC, O, S, NHCO, CONH, C=C, C≡C, an aromatic moiety, substituted $C_{60}$ moiety, N=N, or a heterocyclic moiety.

In a specific embodiment, the porphyrin-based compound comprises a Formula (III) compound with m=2, 3 or 4, n=10, M=2H, Zn or Cu and L=COO, OOC or O.

Examples of preparation of the porphyrin-based compounds are disclosed in U.S. Pat. No. 7,291,727, which is incorporated herein by reference in its entirety.

In illustrative embodiments, the fullerene-based compound may comprise a $C_{60}$, a $C_{70}$, a $C_{76}$, a $C_{84}$, a carbon nanotube, graphene, or any derivative thereof, such as a Formula (V) compound (PCBM) and methanofullerene [6,6]-phenyl-$C_{71}$-butyric acid methyl ester ($PC_{71}BM$):

(V)

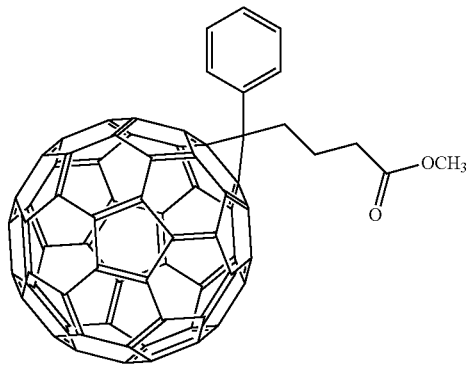

In exemplary embodiments, the preparation of the blend is accomplished by dissolving the donor and the acceptor in a solvent such as tetrahydrofuran (THF), chlorobenene, dichlorobenzene, toluene, xylene, ether, chloroform, N,N-dimethylformamide, and methylene chloride, or a mixture of solvents. If necessary, the mixture may be dissolved with the aid of heating or ultrasonicating. Once a homogeneous solution is obtained, the solvents are removed, rendering a dry product.

The invention further provides various materials and devices such as an organic semiconducting material, a photovoltaic device such as a bulk heterojunction photovoltaic cell, a solar cell, an organic/hybrid photovoltaic cell, a homeotropically aligned blend thin film, a liquid crystalline blend thin film, a photo-sensitive electric resistor, and an organic light emitting device, all of which comprise a liquid crystalline blend as described above. For example, a photovoltaic device may comprise at least one layer which comprises the liquid crystalline blend of the present invention. Highly ordered nanostructured thin films comprising porphyrin and fullerene (or phthalocyanine and fullerene) supramolecular complex can be prepared by simple thermal annealing.

In various embodiments, the invention provides a photovoltaic cell including at least one layer comprising a partially or completely homeotropically aligned discotic LC-fullerene blend sandwiched between at least two substrate layers and a method for fabricating the blended thin film. In specific embodiments, the homeotropically aligned blend according to the invention is included in a photovoltaic cell comprising at least a discotic liquid crystal as an electron donating material and a fullerene material, such as $C_{60}$, $C_{60}$ derivative, $C_{70}$, $C_{70}$ derivative, carbon nanotube or graphene, as an electron accepting material. Such discotic LC may comprise at least a discotic LC porphyrin or phthalocyanine which may contain at least a perfluoroalkyl at the peripheral chain.

Typically, a photovoltaic device comprises a first transparent electrode, a second electrode, and the liquid crystalline blend positioned between the first and second electrodes. The first electrode may be an indium tin oxide electrode coated on a glass or plastic substrate; and the second electrode may comprise aluminum, copper, zinc, silver, gold or titanium dioxide.

In one embodiment, the present liquid crystalline blend is used to form a photovoltaic cell. As seen in FIG. 1, the structure of a photovoltaic cell 10 includes at least one photoactive layer 12 comprising the liquid crystalline blend sandwiched between first 14 and second 16 electrodes, the first of which is transparent or substantially transparent. The electrodes may be positioned on first and second substrates 18, 20. Optionally, the photovoltaic device may include one layer (not shown) consisting of metal nanoparticles or their composites for solar harvesting. In an embodiment, a photoactive heterojunction blend layer is sandwiched between the two electrodes with different work functions. For example, the cell may be a bulk heterojunction cell with the liquid crystalline blend composed of a discotic liquid crystal and one or more other components, which may be any material such as $C_{60}$, its derivative, $C_{70}$, its derivative, a dye or a carbon nanotube.

The electrode material can be, for example, any of platinum, rhodium, metallic ruthenium and ruthenium oxide. Further, conductive materials, such as tin oxide, tin oxide doped with Sb, F or P, indium oxide, indium oxide doped with Sn and/or F, and antimony oxide, having their surfaces overlaid with the above electrode materials by plating or vapor deposition can also be used as the electrode layer. Still further, common electrodes, such as a carbon electrode, can also be used for constituting the electrode layer.

In one embodiment, substrates which are transparent and have insulating properties, such as a glass plate, quartz plate, plastic plate or plates formed from other organic polymers, can be used as the first transparent substrate 18. The transparent electrode positioned on a surface of the transparent substrate can be composed of common electrodes such as those of indium tin oxide (ITO), tin oxide doped with Sb, F or P, indium oxide doped with Sn, Zn and/or F, antimony oxide, zinc oxide and noble metals, which may be coated with a transparent conductive polymer layer for hole collection. The non-transparent substrate 20 may be a combined substrate/electrode and can be formed of metals such as titanium, aluminum, copper, silver, gold and nickel, and which may also be coated with an interface layer; or conducting metal oxide, such as zinc oxide, titanium oxide, etc; or conducting polymer. For example, the photovoltaic device may be composed of an ITO coated transparent electrode and an aluminum, copper, silver or gold coated reflective electrode. In a specific embodiment of the invention, the transparent substrate can be glass or plastic. Alternately, a separate electrode can be positioned on a non-conducting substrate.

A photosensitizing agent can be sorbed (e.g., chemisorbed and/or physisorbed) on the nanoparticles for solar harvesting. The photosensitizing agent may be sorbed on the surfaces of the nanoparticles, within the nanoparticles, or both. The photosensitizing agent is selected, for example, based on its ability to absorb radiation such as photons in a wavelength range of operation (e.g., within the visible spectrum), its ability to produce free electrons (or holes) in a conduction band of the nanoparticles, and its effectiveness in complexing with or sorbing to the nanoparticles. Suitable photosensitizing agents may include, for example, dyes that include functional groups, such as carboxyl and/or hydroxyl groups.

Examples of dyes include black dyes (e.g., tris(isothiocyanato)-ruthenium (II)-2,2':6',2"-terpyridine-4,4',4"-tricarboxylic acid, tris-tetrabutylammonium salt), orange dyes (e.g., tris(2,2'-bipyridyl-4,4'-dicarboxylato) ruthenium (II) dichloride, purple dyes (e.g., cis-bis(isothiocyanato)bis-(2, 2'-bipyridyl-4,4'-dicarboxylato)-ruthenium (II)), red dyes (e.g., an eosin), green dyes (e.g., a merocyanine) and blue dyes (e.g., a cyanine). Examples of additional dyes include anthocyanines, perylenes, porphyrins, phthalocyanines, squarates, and certain metal-containing dyes.

Generally, the method for producing a photovoltaic cell includes the steps of a) providing a first transparent electrode and a second electrode; b) positioning the liquid crystalline blend of the invention between the first and second electrodes; and c) aligning the discotic LC homeotropically.

For example, the two electrodes may be glued or otherwise attached and sealed to form a cell. Depending on the method of filling the cell, a small slit may be maintained for liquid crystal uptake. A typical gap thickness between the two electrodes is about 0.001-10 μm. The liquid crystalline blend is then deposited inside the cell using known methods. After drying the film, the other electrode is laminated on top of the film to form a cell.

In an embodiment, the photovoltaic cell is produced by a method comprising:

a. sealing the first transparent electrode and second electrode together while maintaining an opening between the two electrodes for uptaking the liquid crystalline blend;

b. heating the liquid crystalline blend in a vacuum chamber to melt it;

c. placing the cell in the vacuum chamber to remove air from the cell;

d. dipping the cell opening into the melted blend; and f. reducing the vacuum level in the vacuum chamber to allow the cell to uptake the liquid crystalline blend.

For example, the discotic liquid crystal or its blend may be heated to melting inside a vacuum chamber. The cell is then placed in the vacuum chamber to remove any air inside the cell. To fill the cell, the opening slit of the cell is dipped into the melted material. The vacuum level is then slowly reduced to allow the cell to uptake the material. Of course, other methods of filling the cell are also possible.

In another embodiment, the photovoltaic cell is produced by a method comprising:

a. depositing a layer of the liquid crystalline blend on the first transparent electrode followed by covering a sacrificial layer;

b. inducing the homeotropic alignment of the blend by thermal annealing and/or applying a magnetic field; and c. removing the sacrificial layer, followed by depositing the second electrode or one or more other optional layers and the second electrode.

In still another embodiment, the photovoltaic cell is produced by a method comprising:

a. dissolving the liquid crystalline blend in a solvent;

b. spin-coating the blend solution on the first transparent electrode; and c. depositing the second electrode or one or more other optional layers and the second electrode.

For example, the discotic liquid crystal as the hole-transporting layer and a photosensitizing agent as the electron transporting layer may be prepared in a solvent and spin-coated onto an indium tin oxide electrode. Suitable solvents may be, e.g., water, alcohols, ethers, carbonates such as propione carbonate, phosphoric esters, dimethylformamide, dimethyl sulfoxide, N-methylpyrrolidone, N-vinylpyrrolidone, sulfur compounds such as sulfolane 66, ethylene carbonate, methylene chloride, chloroform, chlorobenzene, toluene, and acetonitrile.

In one embodiment, a small area solar cell can act as a simple photosensor in conjunction with a Schmidt trigger circuit, which can set a tunable threshold voltage for detection and act as a photosensor.

EXAMPLES

The exemplary LC porphyrin was synthesized starting from 1,1,1,2,2,3,3,4,4-nonafluoro-4-iodo-butane by radical addition, reduction, bromination, Williamson ether formation, hydrolysis and esterification, as shown below. Its chemical structure was well identified by $^1H$ NMR, $^{13}C$ NMR, MS, UV-vis and elemental analysis.

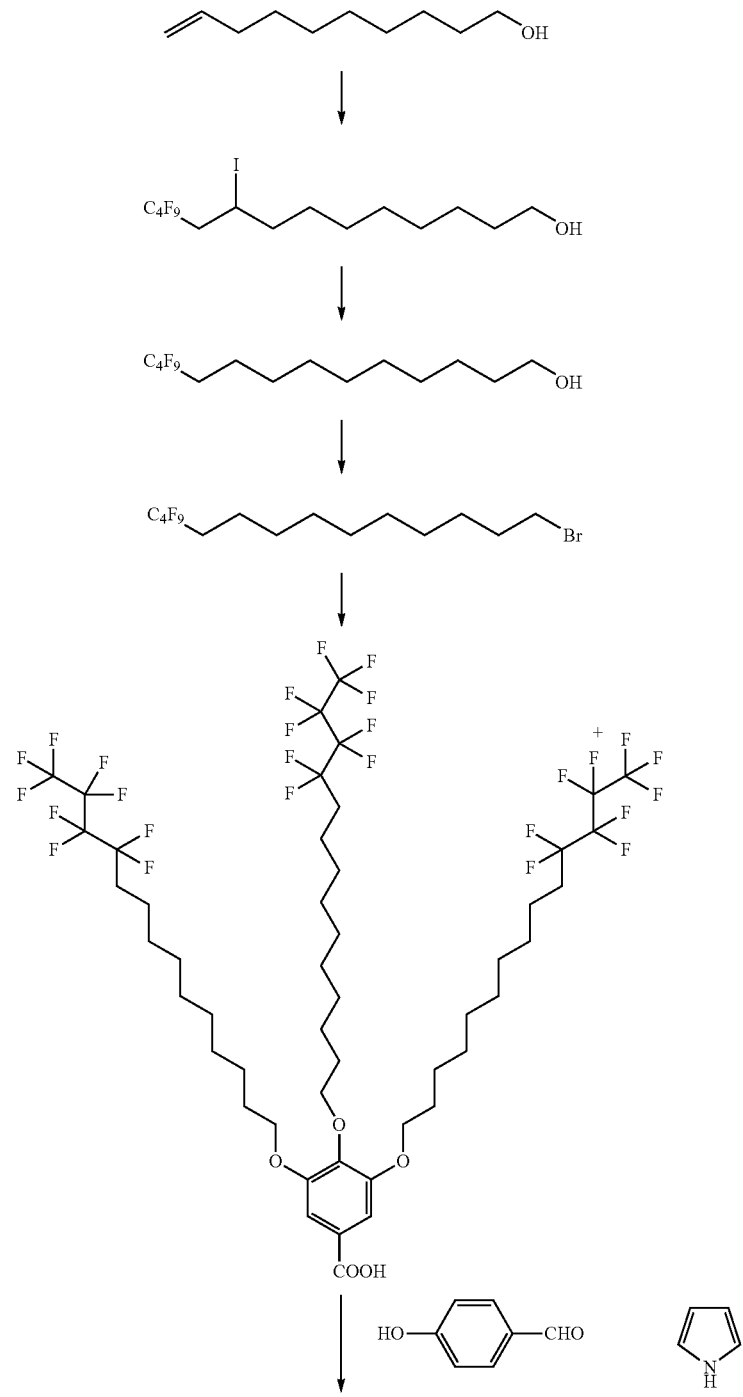

-continued

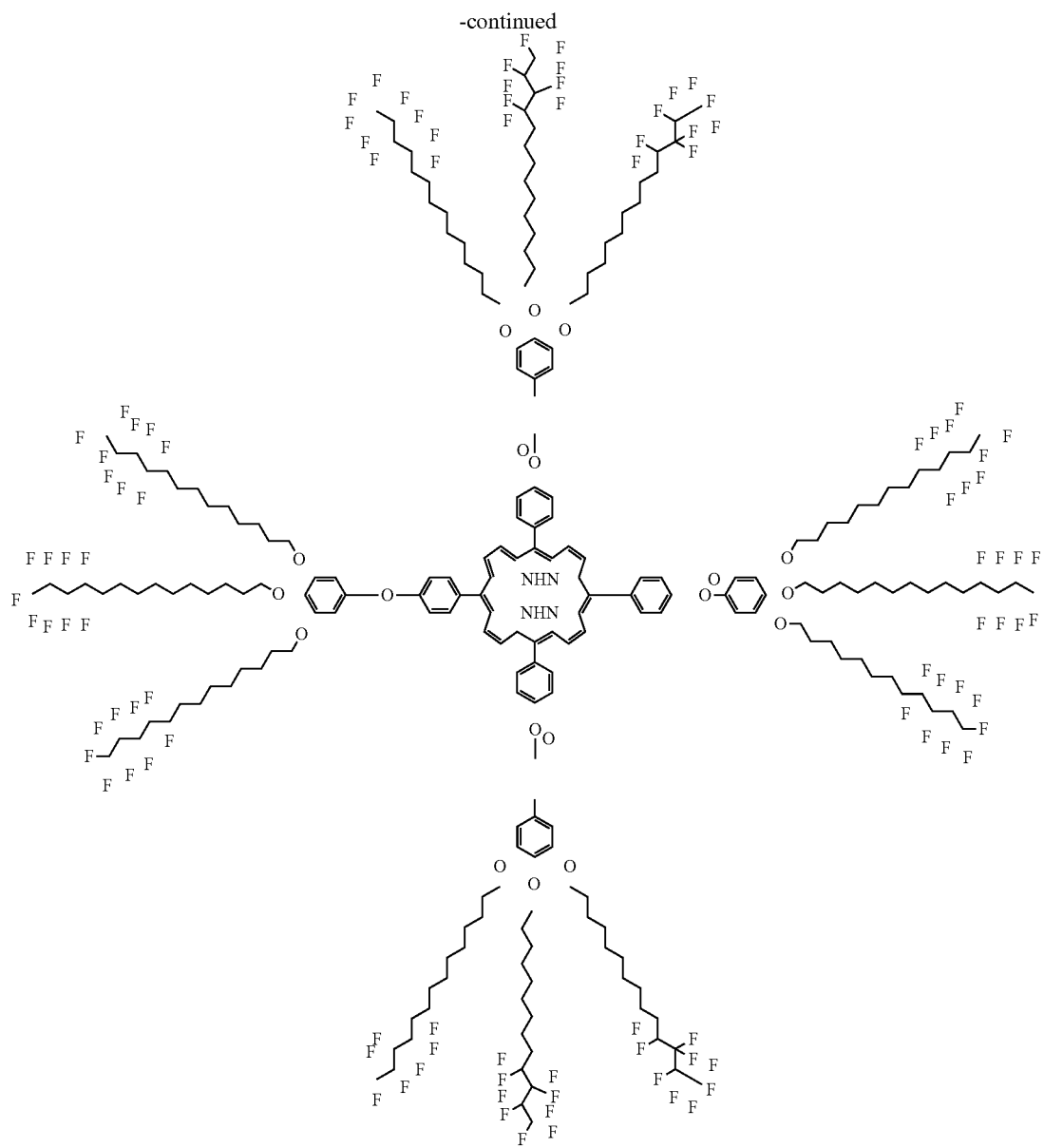

Preparation of the blends with the LC porphyrin and PCBM in a 2:1 molar ratio: The LC porphyrin and PCBM were dissolved in a 2:1 molar ratio in chlorobenzene in an ultrasonic bath. The resulting solution was evaporated to dryness under reduced pressure to get the liquid crystalline blend in a 2:1 molar ratio which can be homeotropically aligned.

The exemplary embodiments have been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A liquid crystalline blend comprising at least an electron donor and at least an electron acceptor, wherein the weight or molar ratio between the electron donor and the electron acceptor is in the range of from about 1:20 to about 20:1; and the electron donor or the electron acceptor is excited by electromagnetic radiation to induce electron transfer between the electron donor and the electron acceptor.

2. The liquid crystalline blend according to claim 1, in which the weight or molar ratio between the electron donor and the electron acceptor is in the range of from about 1:10 to about 10:1.

3. The liquid crystalline blend according to claim 1, in which the weight or molar ratio between the electron donor and the electron acceptor is in the range of from about 1:6 to about 6:1.

4. The liquid crystalline blend according to claim 1, in which the weight or molar ratio between the electron donor and the electron acceptor is in the range of from about 1:2 to about 2:1.

5. The liquid crystalline blend according to claim 1, in which the electron donor, the electron acceptor, or both is (are) halo-substituted.

6. The liquid crystalline blend according to claim 1, in which the electromagnetic radiation is selected from gamma ray, X-ray, UV-Visible light, infrared radiation, and any combination thereof.

7. The liquid crystalline blend according to claim 1, in which the electromagnetic radiation comprises solar light.

8. The liquid crystalline blend according to claim 1, in which a plurality of the electron donors or a plurality of the electron acceptors are self-assembled or self-organized.

9. The liquid crystalline blend according to claim 8, having a columnar liquid crystal phase which is partially or completely homeotropically or homogeneously aligned.

10. The liquid crystalline blend according to claim 8, in which the electron donor or the electron acceptor comprises a π-conjugated structure.

11. The liquid crystalline blend according to claim 8, in which the electron donor comprises a liquid crystal selected from the group consisting of a porphyrin-based compound, a phthalocyanine-based compound, a discotic LC, a polymer, or any combination thereof.

12. The liquid crystalline blend according to claim 8, in which the electron acceptor comprises a fullerene-based compound, a carbon nanotube, a graphene, a photosensitive dye, a thiophene-based material, or any combination thereof.

13. The liquid crystalline blend according to claim 8, in which the electron donor comprises a liquid crystal selected from the group consisting of a porphyrin-based compound, a phthalocyanine-based compound, or a combination thereof; the electron acceptor comprises a fullerene-based compound; and the weight or molar ratio between the electron donor and the electron acceptor is in the range of from about 1:6 to about 6:1.

14. The liquid crystalline blend according to claim 13, in which the weight or molar ratio is in the range of from about 1:2 to about 2:1.

15. The liquid crystalline blend according to claim 11, in which the porphyrin-based compound comprises a Formula (I) compound, and the phthalocyanine-based compound comprises a Formula (II) compound:

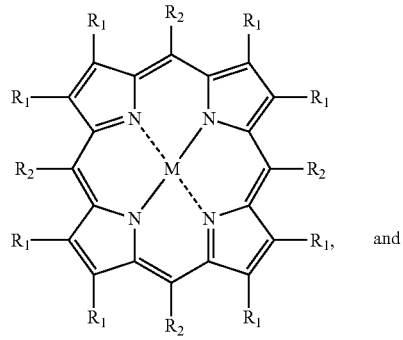

(I)

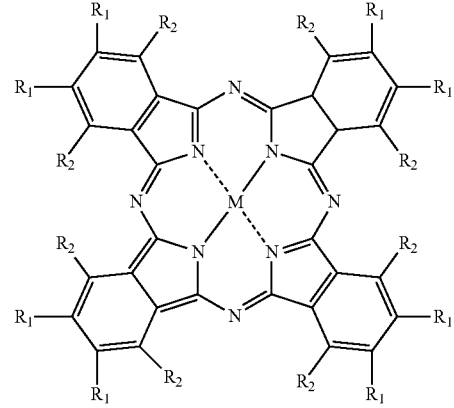

(II)

wherein M =2H, Zn, Co, Cu, Ni, Cr, Mn, Mg, Ce, Ru, Rh, Pt, Au, or a lanthanide metal and which may be bound to halo, O, OH, =CO, amine or heterocylic moiety; and wherein each of $R_1$ and $R_2$ independently of each other comprises an alkyl which may optionally include perfluoroalkyl, aromatic moiety, heterocyclic moiety, substituted $C_{60}$, or one or more of O, S, Br, Cl, CO, COO, NH, C≡C, N=N and/or C=C.

16. The liquid crystalline blend according to claim 11, in which the porphyrin-based compound comprises a Formula (III) compound, and the phthalocyanine-based compound comprises a Formula (IV) compound:

(III)

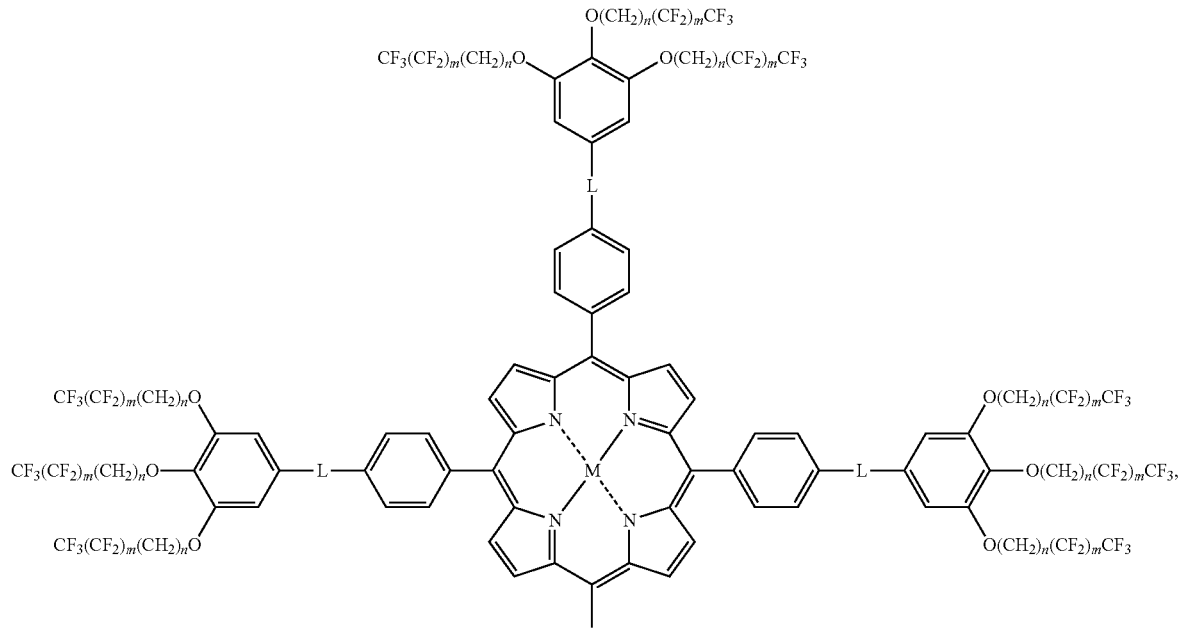

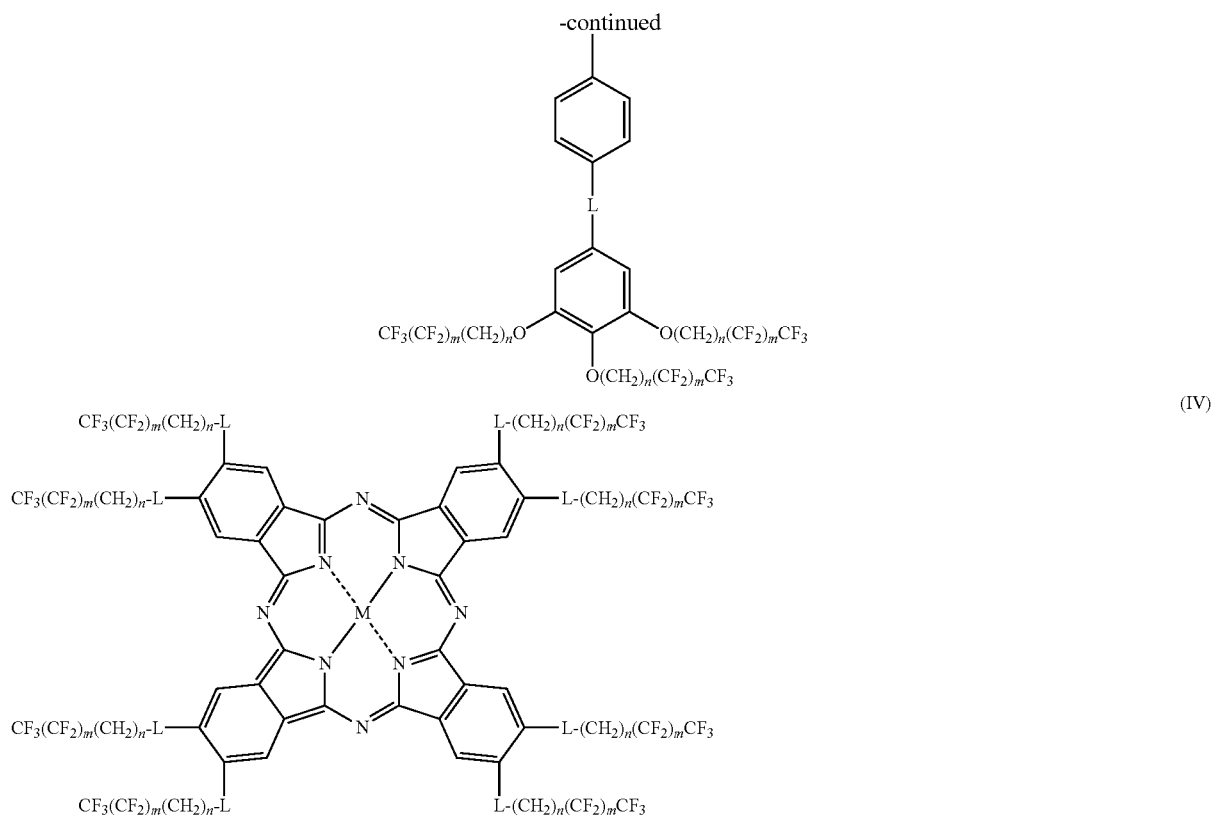

(IV)

wherein m is in the range of 0-20, n is in the range of 3-20, and M is selected from 2H, Cu, Zn, Mg, Co, Ni, Mn, Fe, Ce, Ru, Rh, Pt, Au, or a lanthanide metal and which may be bound to halogen, O, OH, =CO or heterocyclic moiety, and L is a linking group selected from COO, OOC, O, S, NHCO, CONH, C=C, C≡C, an aromatic moiety, substituted $C_{60}$, N=N, or a heterocyclic moiety.

17. The liquid crystalline blend according to claim 16, in which m=3 or 4, n=10, M=2H, Cu or Zn and L=COO, OOC or O in Formula (III).

18. The liquid crystalline blend according to claim 13, in which the fullerene-based compound comprises a $C_{60}$, $C_{70}$, $C_{76}$ and $C_{84}$, a carbon nanotube, graphene, or any derivative thereof such as a Formula (V) compound or methanofullerene [6,6]-phenyl-C71-butyric acid methyl ester ($PC_{71}BM$):

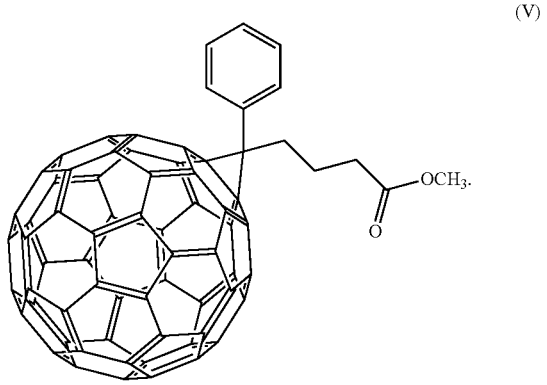

(V)

19. A liquid crystalline blend comprising at least an electron donor and at least an electron acceptor, in which the weight or molar ratio between the electron donor and the electron acceptor is in the range of from about 1:20 to about 20:1, wherein the electron donor, the electron acceptor, or both is (are) halo-substituted; and the electron donor or the electron acceptor is excited by electromagnetic radiation to induce electron transfer between the electron donor and the electron acceptor.

20. The liquid crystalline blend according to claim 19, in which a plurality of the electron donors or a plurality of the electron acceptors are self-assembled or self-organized.

21. The liquid crystalline blend according to claim 19, having a columnar liquid crystal phase which is partially or completely homeotropically or homogeneously aligned.

22. The liquid crystalline blend according to claim 19, in which the electron donor or the electron acceptor comprises a π-conjugated structure.

23. The liquid crystalline blend according to claim 19, in which the electron donor comprises a liquid crystal such as a porphyrin-based compound, a phthalocyanine-based compound, a discotic LC, a polymer, or any combination thereof.

24. The liquid crystalline blend according to claim 19, in which the electron acceptor comprises a fullerene-based compound, a carbon nanotube, a graphene, a photosensitive dye, a thiophene-based material, or any combination thereof.

25. The liquid crystalline blend according to claim 5, wherein the liquid crystalline blend is an organic semiconducting material.

26. The liquid crystalline blend according to claim 5, wherein the blend comprises at least one material of a device which is selected from a photovoltaic device, a bulk heterojunction photovoltic cell, a solar cell, a homeotropically aligned blend thin film, a liquid crystalline blend thin film, a photo-sensitive electric resistor, and an organic light emitting device.

27. The liquid crystalline blend according to claim 26, wherein the device is a photovoltaic device comprising at least one layer which comprises the liquid crystalline blend.

28. The liquid crystalline blend according to claim 27, wherein the device comprises a first transparent electrode, a second electrode, and the liquid crystalline blend is positioned between the first and second electrodes.

29. The liquid crystalline blend according to claim 28, wherein the first electrode is an indium tin oxide electrode coated on a glass or plastic substrate.

30. The liquid crystalline blend according to claim 29, wherein the second electrode comprises aluminum, copper, zinc, silver, gold or titanium dioxide.

31. The liquid crystalline blend according to claim 28, which includes one layer consisting of nanoparticles or their composites for solar harvesting.

32. A method for producing the photovoltaic cell of claim 30, comprising:
   a. sealing the first transparent electrode and second electrode together while maintaining an opening between the two electrodes for uptaking said liquid crystalline blend;
   b. heating the liquid crystalline blend in a vacuum chamber to melt it;
   c. placing the cell in the vacuum chamber to remove air from the cell;
   d. dipping the cell opening into the melted blend; and
   f. reducing the vacuum level in the vacuum chamber to allow the cell to uptake the liquid crystalline blend.

33. A method for producing the photovoltaic cell of claim 30, comprising:
   a. depositing a layer of said liquid crystalline blend on the first transparent electrode followed by covering the layer of liquid crystalline blend with a sacrificial layer;
   b. inducing the homeotropic alignment of the blend material by thermal annealing and/or applying a magnetic field; and
   c. removing the sacrificial layer followed by depositing the second electrode or one or more other optional layers and the second electrode.

34. A method for producing the photovoltaic cell of claim 30, comprising:
   a. dissolving said liquid crystalline blend in a solvent;
   b. spin-coating the blend solution on the first transparent electrode; and
   c. depositing the second electrode or one or more other optional layers and the second electrode.

* * * * *